United States Patent [19]

Terstappen et al.

[11] Patent Number: 5,057,413

[45] Date of Patent: Oct. 15, 1991

[54] METHOD FOR DISCRIMINATING BETWEEN INTACT AND DAMAGED CELLS IN A SAMPLE

[75] Inventors: Leon W. M. M. Terstappen, Los Altos; Michael R. Loken, Palo Alto; Virendra O. Shah, Santa Clara, all of Calif.

[73] Assignee: Becton, Dickinson and Company, Franklin Lakes, N.J.

[21] Appl. No.: 206,454

[22] Filed: Jun. 13, 1988

[51] Int. Cl.$^5$ .................... C12Q 1/68; C12Q 1/02; C12Q 1/04; G01N 33/535

[52] U.S. Cl. .................... 435/6; 435/7.1; 435/7.2; 435/29; 435/34; 436/63; 436/17.2; 436/800

[58] Field of Search ............ 435/9, 6, 7, 29, 257, 435/810; 436/63, 94, 172, 43, 548, 800; 530/380; 250/459.1, 461.2

[56] References Cited

U.S. PATENT DOCUMENTS

| | | | |
|---|---|---|---|
| 3,826,364 | 7/1974 | Bonner et al. | 209/3 |
| 4,094,745 | 6/1978 | Scholefield | 435/6 |
| 4,284,412 | 8/1981 | Hansen et al. | 23/230 |
| 4,520,110 | 5/1985 | Stryer et al. | 436/501 |
| 4,544,546 | 10/1985 | Wang et al. | 424/7.1 |
| 4,585,736 | 4/1986 | Dolbeare et al. | 436/94 |
| 4,661,913 | 4/1987 | Wu et al. | 364/500 |
| 4,727,020 | 2/1988 | Recktenwald | 435/6 |

FOREIGN PATENT DOCUMENTS

| | | | |
|---|---|---|---|
| 0121262 | 10/1984 | European Pat. Off. | 436/172 |
| 0212455 | 3/1987 | European Pat. Off. | 250/461.2 |

OTHER PUBLICATIONS

Jackson et al., Manual of Clinical Laboratory Immunology, (3rd Edition), 1986 pp. 226-235.
Herzenberg et al., Fluorescence Activated Cell Sorting, Sci. Am., 234:108 (1976).
Terstappan et al., Discriminating Between Damaged and Intact Cells in Fixed Flow Cytometric Samples, Cytometry, 9:477 (1988).
Practical Flow Cytometry, Shapiro, pp. 125-150 (Id. Ed., 1988) Alan R. Liss, Inc.
Rabinovitch et al., Journal of Immunology, 136:2769 (1986).

*Primary Examiner*—Esther L. Kepplinger
*Assistant Examiner*—Toni Scheiner
*Attorney, Agent, or Firm*—Robert M. Hallenbeck

[57] ABSTRACT

A method is disclosed for the discrimination between intact and damaged cells in a sample, and more particularly, the method uses a vital nucleic acid dye to selectively stain intact versus damaged cells which then may be counted and sorted by flow cytometry means. The method also may be used in conjunction with fluorescently labelled monoclonal antibodies to simultaneously identify cellular antigens.

10 Claims, 12 Drawing Sheets

ORTHOGONAL LIGHT SCATTERING

FORWARD LIGHT SCATTERING

LDS-751

FORWARD LIGHT SCATTERING

ORTHOGONAL LIGHT SCATTERING

FORWARD LIGHT SCATTERING

ORTHOGONAL LIGHT SCATTERING

LDS-751

LDS-751

ORTHOGONAL LIGHT SCATTERING

FORWARD LIGHT SCATTERING

LDS-751

FORWARD LIGHT SCATTERING

LDS-751

FDA

ORTHOGONAL LIGHT SCATTERING

LDS-751

ORTHOGONAL LIGHT SCATTERING

ORTHOGONAL LIGHT SCATTERING

ORTHOGONAL LIGHT SCATTERING

ORTHOGONAL LIGHT SCATTERING

FORWARD LIGHT SCATTERING

METHOD FOR DISCRIMINATING BETWEEN INTACT AND DAMAGED CELLS IN A SAMPLE

FIELD OF THE INVENTION

This invention relates to a method for discriminating between intact and damaged cells in a sample, and more particularly, relates to a method for discriminating between intact and damaged cells in a peripheral blood sample, wherein the intact and damaged cells are discriminately stained by a nucleic acid stain.

BACKGROUND OF THE INVENTION

The detection and identification of cell types in the hematopoietic system has long been a useful research and clinical tool. A number of automated methods exist to aid the researcher and clinician. Among those methods include flow cytometry and fluorescence microscopy. In recent years, the former method has become increasingly sophisticated and has become generally accepted as a tool to aid in the identification of or discrimination between cell types and between various functional and/or maturational subsets within a cell type.

Flow cytometers, which are more generally described in U.S. Pat. Nos. 4,661,913, 4,284,412 and 3,826,364, and in an article by Herzenberg et al., Sci. Am., 234:108 (1976), have been used to identify different populations of leukocytes in a heterogeneous sample by detecting multiple independent parameters on individual cells that pass through the sensing region. Typically, these parameters include forward light scatter (FLS, which is a measure of relative particle size), orthogonal light scatter (OLS, which is a measure of relative granularity) and fluorescence. Fluorescence may be measured from cells that incorporate a nucleic acid or other vital stain or may be measured from cells bearing surface markers which are labelled with monoclonal antibodies (MAbs) that are conjugated directly or indirectly to fluorochromes as described, for example, in U.S. Pat. No. 4,520,110. By combining and comparing these parameters, the various leukocyte components may be distinguished.

U.S. Pat. No. 4,727,020 provides one example of how a flow cytometer operates and may be used to identify leukocyte subpopulations. Unlysed whole blood was treated with one MAb conjugated to phycoerythrin (PE) specific for CD4+ T cells and and a second MAb conjugated to fluoroscein isothiocyanate (FITC) specific for CD8+ T cells. A nucleic acid dye, LDS-751 TM (Exciton), was added to identify nucleated leukocytes. The labelled cells then were analyzed by flow cytometry. A gate was set for LDS-751+ cells (i.e., for nucleated leukocytes, thereby excluding erythrocytes and platelets). The method allowed separation of leukocyte subpopulations by comparing the various parameters measured.

One problem inherent in any method that makes use of fluorescently labelled MAbs and/or nucleic acid dyes, however, is the propensity of the labels to indiscriminantly bind to damaged cells or cell debris in a sample. This problem is compounded by the fact that in order to prepare cells for labelling, the cells must undergo several preparation techniques, all of which increase the number and proportion of cells that become damaged or ruptured in any one sample. These damaged cells and associated cell debris and their accompanying fluorescence must be discriminated against in the overall sample in order to thoroughly examine the remaining intact cells. Depending upon the method used to prepare the cells in any one sample and even between samples using the same method, sample preparation can introduce a significant amount of variation into the system. As a result, method used for immunofluorescence analysis of cells could mis-identify damaged cells as part of the subpopulations of interest.

A variety of techniques exist for determining whether a cell in a sample is intact or damaged. Viable, intact cells can be distinguished from dead cells by using either fluoroscein diacetate (FDA) or propidium iodide (PI). In these methods, the sample is treated with either FDA or PI and then examined for fluorescence. Cells that stain with FDA are considered "viable"; cells that stain with PI are considered "dead." The methods are limited, however, in that the cells cannot be fixed if the stains are to be used to identify viable cells. Another limitation on the use of FDA is that it brightly fluoresces so that it overwhelms the immunofluorescence signals from other stains, such as FITC and PE, rendering them unreadable.

Other methods to detect intact cells that do not make use of such dyes also exist. FLS, on a flow cytometer for example, may be used to discriminate between intact and damaged cells but only if the cells in the sample are derived from a homogeneous population. Cells from a heterogeneous population cannot be so distinguished because of variations in cell size and light scattering properties.

Each of the above-described methods suffers from some defect that makes it inapplicable as a general method for discrimination between damaged and intact cells in a heterogeneous sample. As a result, there is no single method that allows the researcher or clinician to examine a heterogeneous cell sample from an individual and to discriminate between damaged and intact cells therein.

SUMMARY OF THE INVENTION

The present invention comprises a method to discriminate between intact and damaged cells in a body fluid sample. The method comprises the steps of: 1) taking a body fluid sample from an individual; 2) adding a nucleic acid dye to said sample; and 3) analyzing the cells in said sample in an automated instrument capable of passing said cells through a sensing region substantially one at a time and capable of detecting and recording both fluorescence and light scattered by individual cells.

In the preferred embodiment, the body fluid sample comprises peripheral whole blood wherein the erythrocytes are lysed, and the nucleic acid dye comprises a stain with a preference for DNA and which also distinguishes between damaged and intact cells based on the amount of fluorescence emitted. It will be appreciated by those skilled in the art that this method also is particularly useful when combined with other methods used to identify cell types (e.g., when fluorescently labelled MAbs are used). Examples of such other methods include those described in U.S. Pat. No. 4,599,304 for the monitoring of activated cells. In such cases, it will be further appreciated that the peak emission spectra of each of the fluorochromes used to label the MAbs and of the nucleic acid dye must be sufficiently distinct so as not to overlap. Similarly, it is desirable that all of the fluorescent labels be excitable at the same wavelength.

This will allow the use of a single laser source in the flow cytometer, as opposed to having a dual laser source as described in U.S. Pat. No. 4,727,020.

A kit comprising a set of containers separately containing a nucleic acid dye and one or MAbs also is disclosed.

DETAILED DESCRIPTION OF THE INVENTION

Figure 1A:
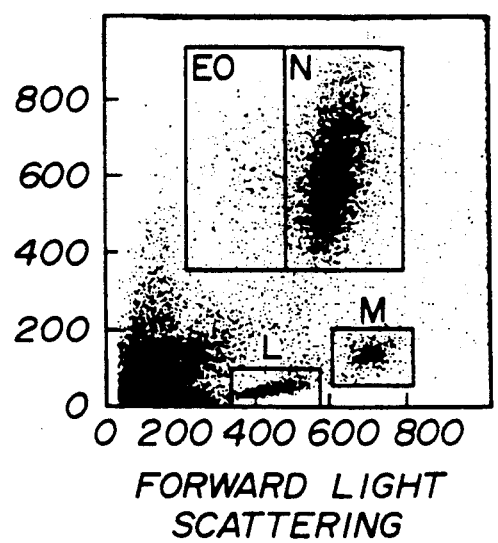
FIGS. 1A-1E comprise several correlations of "dot" plots of OLS vs. FLS (A,C-E) and log LDS-751 fluorescence vs. FLS (B) for fixed PBL (peripheral blood leukocytes) from erythrocyte depleted whole blood.

The present invention comprises a method for the discrimination between and identification of cell types in a body fluid. Preferably, the body fluid is erythrocyte depleted peripheral blood; however, other body fluids that may be sampled include peritoneal, spinal and brain fluids, as well as urine. In addition, cell suspensions of bone marrow, lymph node, liver, spleen and thymus may be used.

The method comprises the steps of:

1) taking a body fluid sample from an individual;

2) adding a fluorescent nucleic acid dye to said sample; and 3) analyzing the cells in said sample in an automated instrument capable of passing said cells through a sensing region substantially one at a time and capable of detecting and recording both fluorescence and light scattered by each of the cells that pass through the sensing region.

The method may be broadened to include a step wherein MAbs are added to the sample prior to staining with the nucleic acid dye. One or more MAbs may be used to detect cell surface antigens or the cells in the body fluid sample. The method is not limited by the MAb used or the cell surface antigen to be detected; however, certain pairs of MAbs are useful in the practice of this invention and include those pairs described in U.S. Ser. No. 126,333, filed Nov. 30, 1987 (commonly assigned to Becton, Dickinson and Company). The MAbs may be directly or indirectly labelled by one or more fluorochromes by methods known to those skilled in the art. It is preferable that the MAbs are directly labelled. It also is preferable that the peak emission spectra of the fluorochromes and the nucleic acid dye all be distinguishable. Further, it is desirable, when a single laser source is used in the automated instrument, to have all the fluorescent materials excitable at substantially the same wavelength (e.g., 488 nm when an argon laser is used). If a dual laser source is used, the excitation spectra may differ.

Desirably, the nucleic acid dye has a preference for DNA which has different fluorescence intensities for intact and damaged cells. In this manner, non-nucleated cells, such as erythroyctes and platelets, will not be stained (or will be stained minimally) such that nucleated cells (e.g., leukocytes) can be distinguished from non-nucleated cells based upon the intensity of fluorescence. In the preferred embodiment, the dye is LDS-751; however, other dyes having a preference for DNA also may be used such as those disclosed in U.S. Pat. No. 4,544,546. Representative nucleic acid dyes include dyes of the following formula

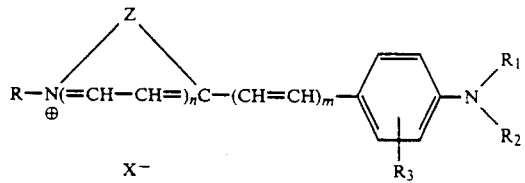

wherein n represents an integer having a value of 0 or 1;

m represents an integer having a value of 1 or 2;

R represents a member selected from the group consisting of lower alkyl, lower hydroxyalkyl, dialkylaminoalkyl, pyrrolidinoalkyl and morpholinoalkyl;

$R_1$ and $R_2$ each represent members selected from the group consisting of hydrogen, lower alkyl and lower haloalkyl;

$R_3$ represents a member selected from the group consisting of hydrogen, lower alkoxy, lower alkyl and amino;

Z represents nonmetallic atoms necessary to complete a heterocyclic nucleus selected from the group consisting of a benzothiazole nucleus, indolenino nucleus, napthothiazole nucleus, benzoselenazole nucleus, benzoxazole nucleus, quinoline nucleus, and pyridine nucleus any of which may be substituted with lower alkyl, halo, nitro, amino and dialkylamino; and X represents an anion. The amount of dye used and the time the cells are stained with the dye should be sufficient to avoid differential staining as a result of kinetic phenomena. Twenty-four hours is more than sufficient time.

A variety of devices may meet the requirements of the automated instrument. Desirably, the instrument comprises a flow cytometer with a single laser source, Preferably, the single laser source is an argon laser tuned to 488 nm. The flow cytometer may further comprise data storage and analyses means such as a personal computer with software sufficient to list, store and analyze at least five parameters of data in various paired combinations. Examples of flow cytometers useful in the practice of this invention include FACS 440 ™, FACScan ™ and FACStar ™ (all commercially available from Becton Dickinson Immunocytometry Systems (BDIS)). Examples of personal computers and appropriate software include Consort 30 ™ data management systems (BDIS) and FACScan RESEARCH or PAINT-A-GATE ™ software (BDIS).

It will be appreciated by those skilled in the art that a fluorescence microscope may be substituted for the automated instrument. In this case, manual counting and identification of cells is required.

EXAMPLES

Peripheral blood of healthy individuals was collected by venipuncture into VACUTAINER ™ blood collection tubes containing ethylenediaminetetracetate as anticoagulant (Becton Dickenson). Erythrocytes were lysed with $NH_4Cl$. One volume of blood was mixed with 15 volumes of 1% $NH_4Cl$ in $H_2O$(pH 7.3) and gently mixed. Cells were lysed for 3-5 minutes, and centrifuged at 200 g for 5 minutes at room temperature. The pellet was resuspended in a volume of a human cell culture medium which is available commercially as RPMI 1640 ™ (Whittaker) 14 times larger than the original blood volume and centrifuged at 200 g for 5 minutes. This washing step was repeated twice and the cells were finally resuspended in phosphate buffered saline containing 1% bovine serum albumin, $10^4$IE penicillin/ml, 100 u/ml streptomycin and 20 mM Hepes (pH 7.3) (PBS). The cell concentration of the remaining peripheral blood leukocytes (PBL) was adjusted to $1 \times 10^7$/ml.

Where MAbs were added to the sample, twenty ul of a pretitered MAb was added to 100 ul of cell suspension. After incubating for 20 minutes on ice, the cells were washed twice with 2 ml of the PBS solution of 4° C. The staining procedure was repeated for a second MAb, if any. The pellet of the immunofluorescent labelled cells was resuspended in 1 ml of 1% paraformaldehyde in PBS.

A stock solution of LDS-751 was made by dissolving 0.2 mg in 1 ml of methanol. A working solution containing 0.5 ml of the stock solution was diluted into a final volume of 50 ml PBS containing 0.1% azide. Ten ul of the LDS-751 working solution was added to the paraformaldehyde fixed cells and kept overnight before flow cytometric analysis. The cell suspension could be kept at least two weeks without changes in the light scattering properties or fading of the immunofluorescence signals on the cells.

In the experiments correlating the fluorescence signals obtained from LDS-751 and FDA, the $NH_4Cl$ lysed cells were resuspended in RPMI 1640 to a final concentration of $1 \times 10^6$/ml Before analysis, the cells were kept one hour in the RPMI solution in order to obtain optimal light scattering properties of the cells. The FDA stock solution was made by dissolving 5 mg FDA in 1 ml of acetone. The FDA working solution contained 5 ul of the stock solution diluted into a final volume of 5 ml PBS containing 0.1% azide. Fifteen minutes before analysis, 30 ul of the FDA working solution was added to 1 ml of the cell suspension together with LDS-751 in a final concentrations of 0.2 ug/ml for the fresh and 0.1 ug/ml for the 48 hours old samples respectively.

The MAbs FITC labelled Leu-Ml. (BDIS) and PE labelled CD11b (Anti-Leu-15, BDIS) were used. With this combination NK-cells and different maturational stages of monocytes and neutrophilic granulocytes could be identified. The MAbs FITC labelled CD20 (Anti-Leu-16, BDIS) and PE labelled CD5 (Anti-Leu-1, BDIS) also were used.

Flow cytometric analyzes were performed on a FACScan ™ flow cytometer. This instrument used an air-cooled Argon ion laser as a light source. The laser operated at 488 nm with an intensity of 15 mW. The laser was focused on the cell stream by means of a prismatic expander and a planoconvex lens providing a 20 um $\times$ 64 um elliptical beam. The optical measurements were performed in a quartz flowcell with a 430 um $\times$ 180 um rectangular flowchannel. A stable flow was achieved by pressurizing sheet and sample flow. Measurements were performed at a sample flow rate of 60 ul/min.

The light scattered in forward direction was collected with a spherical lens provided with a rectangular beam stop (collecting angles 1-10 degrees) and detected by a solid state silicon detector. Orthogonal scattered and fluorescence light was collected by a lens (H 94, 1.22 NA) coupled to the flowcell with an optical gel (collecting angles between 23° and 157°). The light was directed to 4 photomultiplier tubes using appropriate optical filter combinations. The fluorescence signals were collected through a 530 nm band pass filter for the FITC signals, a 585 nm band pass filter for the PE signals and a 650 nm longpass filter for the fluorescent light obtained from LDS-751. The scattered light was directed to a photomultiplier using a Brewster angle beam splitter.

The five parameters were digitized and stored in memory by Direct Memory Access in the list mode with Consort 30 ™. Each measurement contained 22,000 cells. Data acquisition was performed with the FACScan Research Software.

Cell sorting was performed on a FACStar ™ flow cytometer. For each population 10,000 cells were sorted into RPMI containing 10% Fetal Calf Serum (FCS). The sorted cells were spun down for 5 minutes at 200 g and resuspended in 100 ul RPMI 1640 containing 10% FCS. Cytospin preparations were made with a Shandon Cyto-centrifuge (Southern Product Ltd., Astmoor, England). The slides were stained with Wright Stain and examined with a light microscope.

EXAMPLE I

Discrimination of Intact From Damaged Cells After Fixation

PBL were obtained by lysing the erythrocytes with $NH_4CL$ as described. These cells were labelled with PE and FITC labeled MAbs following standard immunofluorescence procedures. After washing, the cells were fixed in 1% paraformaldehyde and the nucleic acid dye, LDS-751, then was added to the cells.

The instrument threshold was set at a low level on the forward angle light scattering channel in order to include platelets and cell debris in the analysis. See FIG. 1A. The major leukocyte cell populations including lymphocytes, monocytes, granulocytes, and the eosinophils (L,M,N,EO respectively, FIG. 1A) could be distinguished from the platelets and cell debris by forward and orthogonal light scattering signals.

Figure 1B:
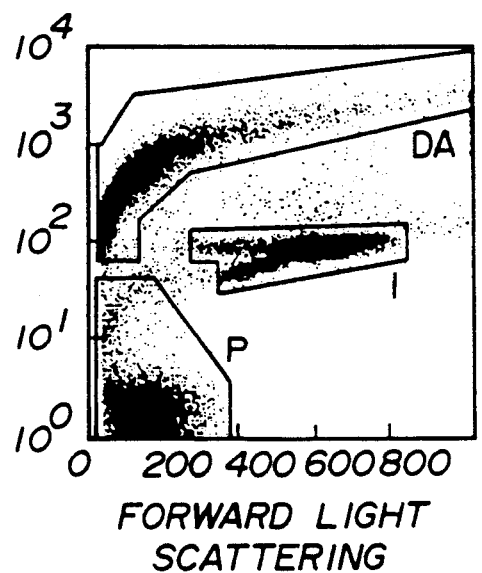

In the correlation between the forward light scattering and LDS-751 fluorescence, FIG. 1B, a population of intermediate staining cells with significant light scattering was identified. See Population I, FIG. 1B. This population included all of the intact cells as identified by forward and right angle light scattering. See FIG. 1D. The population with the highest amount of LDS-751 fluorescence, DA in FIG. 1B, had low to intermediate amounts of forward and orthogonal light scattering. See FIG. 1C. The proportion of events within Population DA varied from sample to sample and differed with changes in preparation procedures. The low light scattering signals and the sample to sample variations suggested that these events were cell debris. This was confirmed by sorting the cell populations identified in FIG. 1B. The cells in Population I were intact cells by microscopic examination. The cells represented within DA were damaged cells, bare nuclei, or aggregated platelets. The particles identified within Population P were platelets and erythrocytes. This latter population had light scattering characteristics shown in FIG. 1E.

Figure 1C:
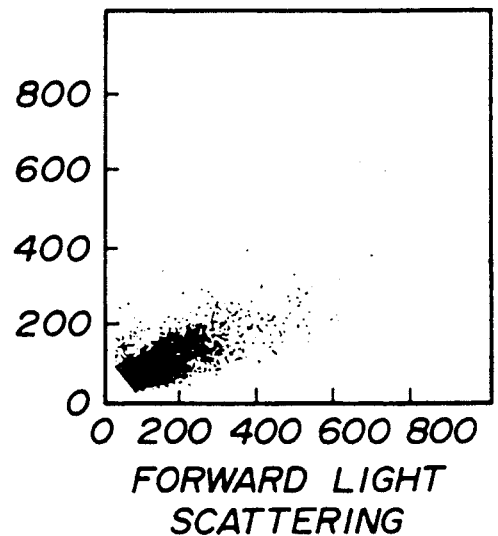

A comparison of FIG. 1C and D would suggest that the use of light scattering alone would include some damage cells with the intact cell populations. The contribution of damaged cells to the populations identified solely by light scattering was determined for twenty normal donors (Table I).

TABLE I

Enumeration of Percentage of Intact Nucleated Cells of 20 Donors Determined by LDS-751 Fluorescence[a]

|  | MIN | MAX | MEAN | S.D. |
|---|---|---|---|---|
| Intact Nucleated Cells[b] | 13 | 66 | 34 | 14.6 |
| Light Scattering gate for[c] | | | | |
| Intact Lymphocytes | 78 | 99 | 88 | 7.1 |
| Intact Monocytes | 8 | 88 | 56 | 21.4 |
| Intact Neutrophils | 47 | 91 | 76 | 11.4 |
| Intact Eosinophils | 11 | 78 | 41 | 16.7 |

Figure 1D:
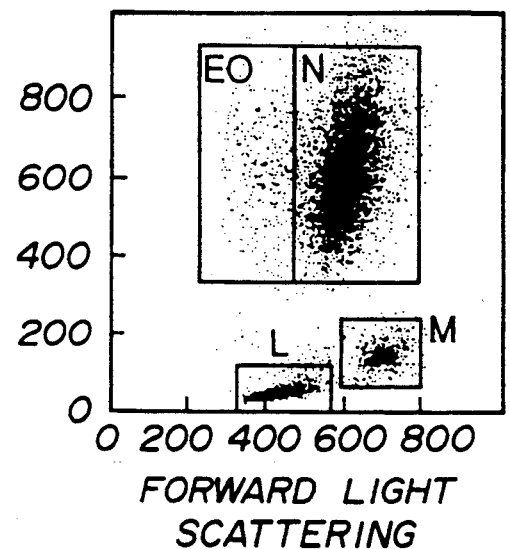

[a]PBL obtained by NH4Cl lysing, fixed in 1% paraformaldehyde and stained with LDS-751.
[b]Cells occurring the region indicated by "I" in FIG. 1B (% is obtained by dividing their number by the total number of nucleated cells (i.e., I + DA) × 100%).
[c]Number of intact nucleated cells occurring in the light scattering gates typical for cell types as indicated in FIG. 1D divided by the number of cells occurring in identical gates set in FIG. 1A × 100%.

Figure 1E:
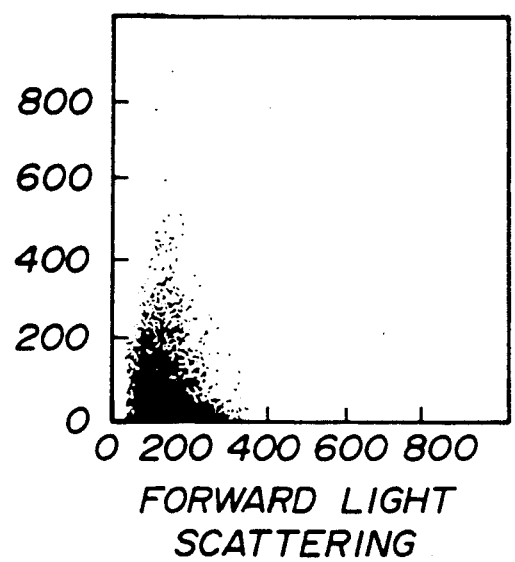

To determine the percentage of cells which might interfere with the immunofluorescence, the percent of intact cells was determined in the light scattering regions typical for lymphocytes, monocytes, neutrophil granulocytes, and eosinophilic granulocytes (FIG. 1D: L,M,N,EO respectively). This table indicates that only a minority of cells (mean 34% intact nucleated cells) survived the sample preparation protocol. In addition, a significant fraction of these damaged cells could not be removed based on light scattering characteristics only. For example, within the lymphocyte light scattering gate (FIG. 1D: L) an average of only 88% of the cells were intact based on LDS-751 fluorescence. It should be noted that erythrocytes which survived the lysis protocol could appear in the light scattering region typical for nucleated cells. (FIG. 1E). By using the additional fluorescence parameter the cells were confined to Population P, FIG. 1B since they did not stain with LDS-751 and therefore could be distinguished from nucleated cells.

EXAMPLE II

Detection of Viable Cells

The extension of this technique to unfixed, viable samples added further confirmation that the LDS-751 was able to discriminate intact from damaged cells. LDS-751 can be used to stain viable leukocytes. This permits the correlation of LDS-751 staining with conventional dyes which assess viability in unfixed samples.

Figure 2A:
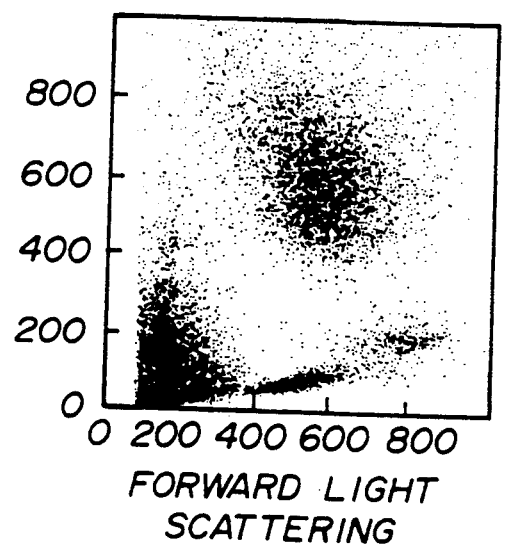
FIGS. 2A-2E comprise several dot plots of OLS vs. FLS (A,D), log LDS-751 fluorescence vs. FLS (B) and vs. log FDA fluorescence (C,E) the PBL were not fixed.
Figure 2B:
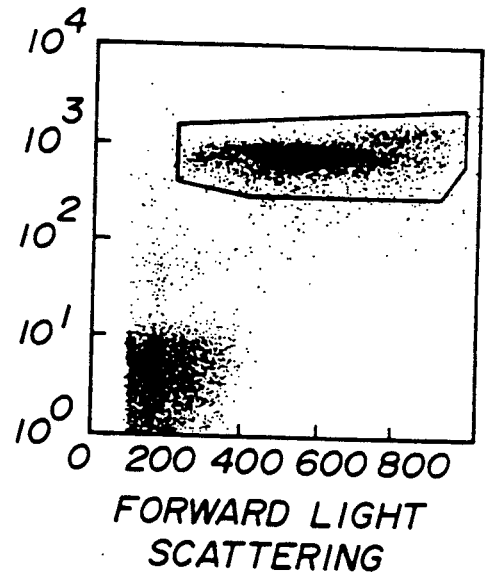
Figure 2C:
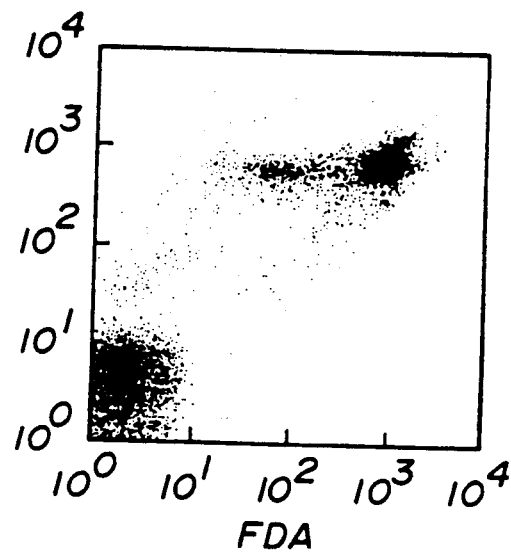
Figure 2D:
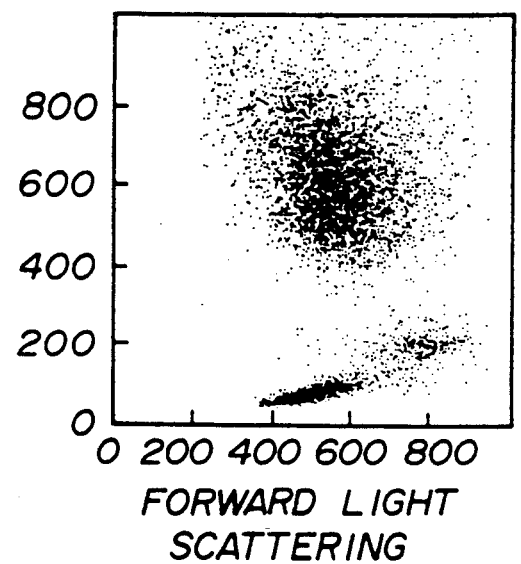
Figure 2E:
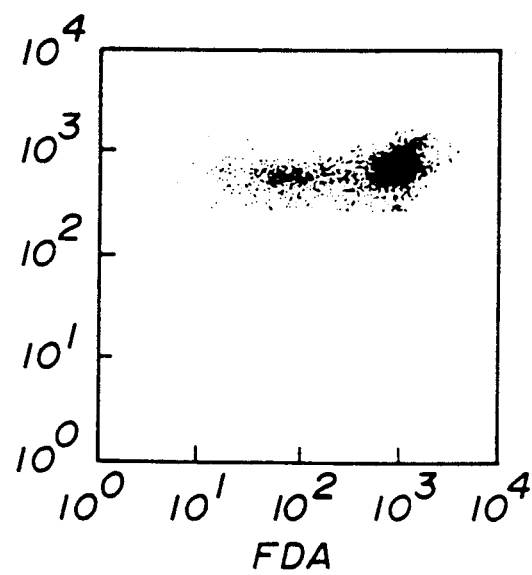
Figure 3A:
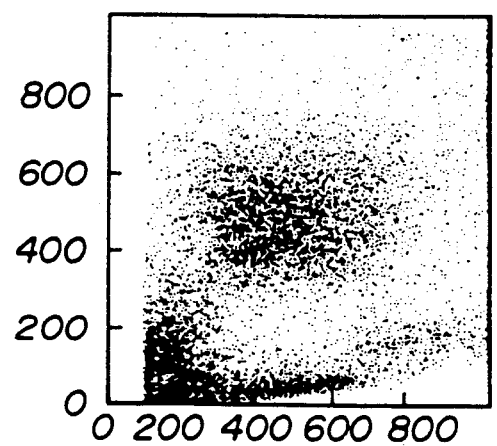
FIGS. 3A-3E comprise several dot plots as in FIG. 2 for cells prepared from the same individual as in FIG. 2, but the cells were held for 48 hours prior to staining with LDS-751 and FDA.
Figure 3B:
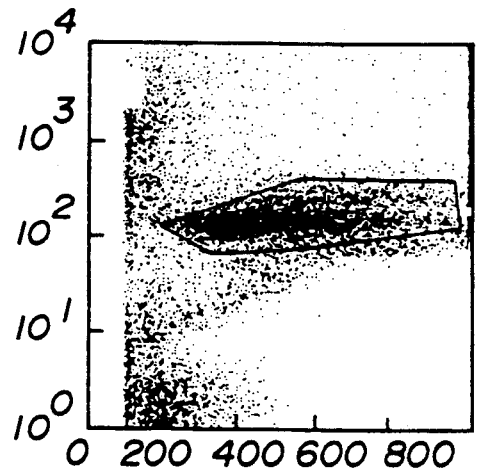
Figure 3C:
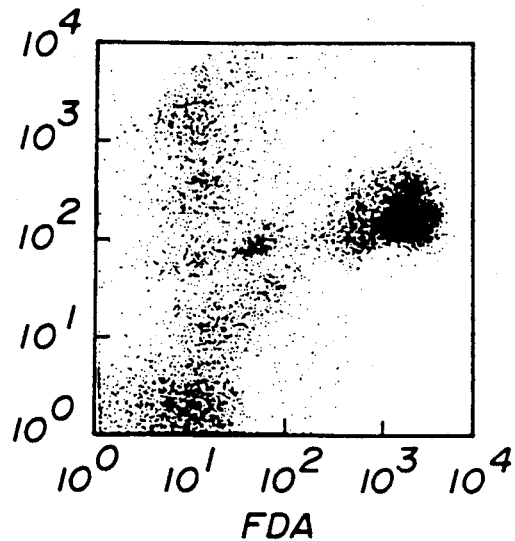
Figure 3D:
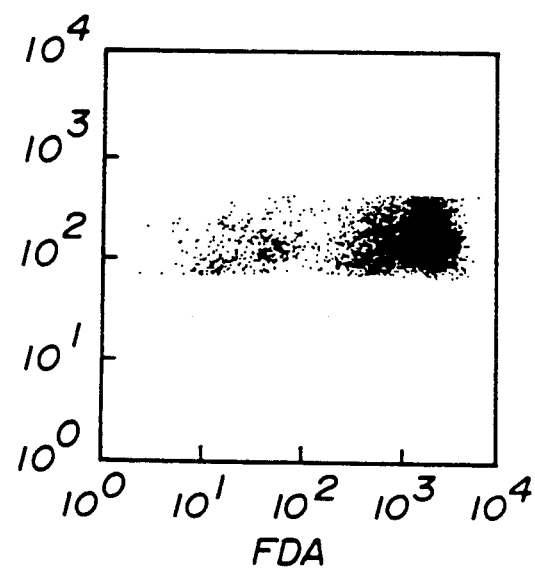
Figure 3E:
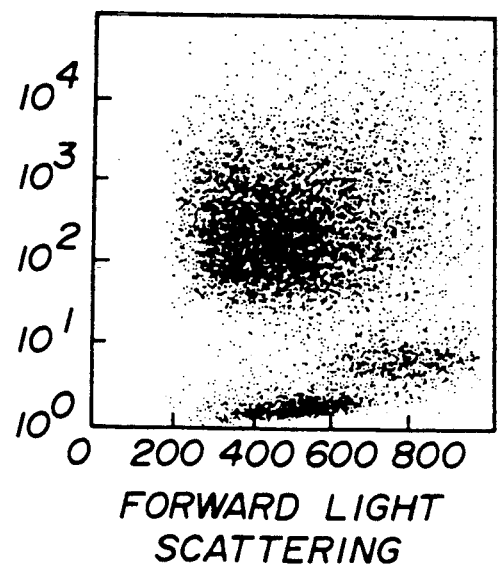
Figure 4A:
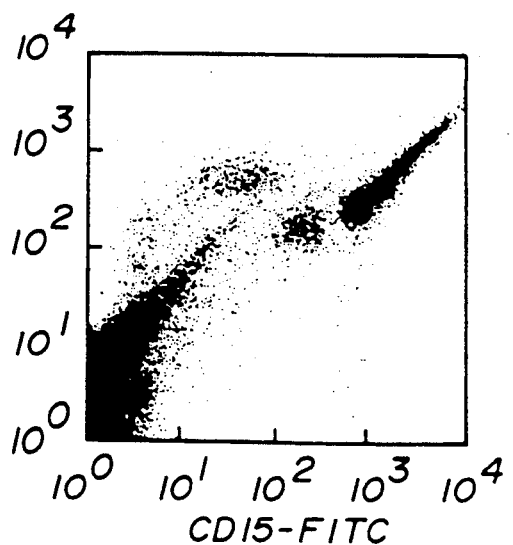
FIGS. 4A-4E comprise several dot plots of log CD5(PE) fluorescence vs. CD20(FITC) fluorescence (A,C,E), log LDS-751 fluorescence vs. FLS (B) and FLS vs. OLS (D) for erythrocyte depleted whole blood which had been reacted with these two MAbs.
Figure 4B:
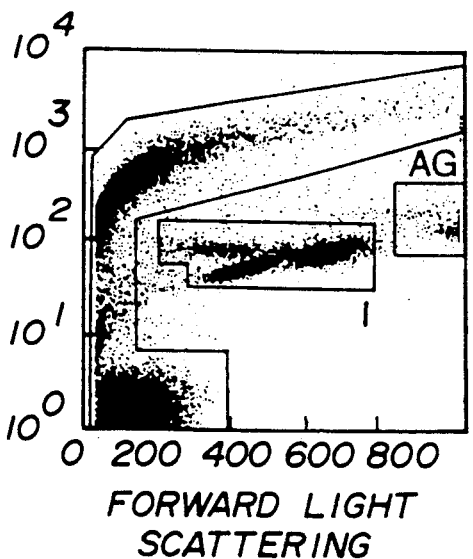
Figure 4C:
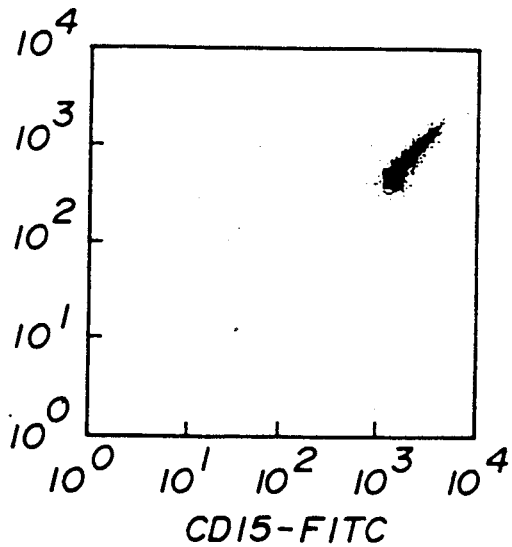
Figure 4D:
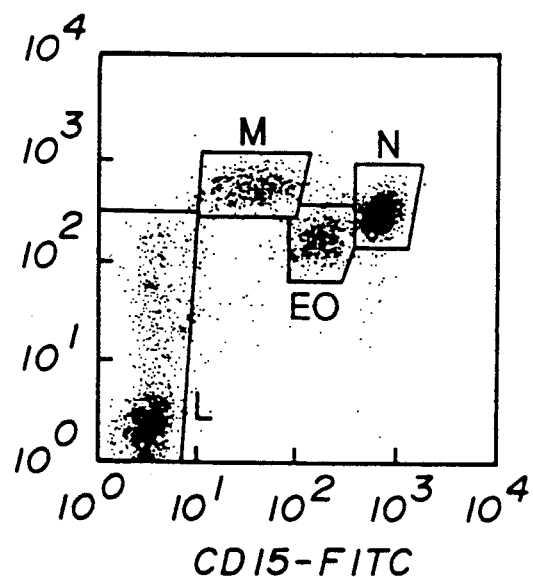
Figure 4E:
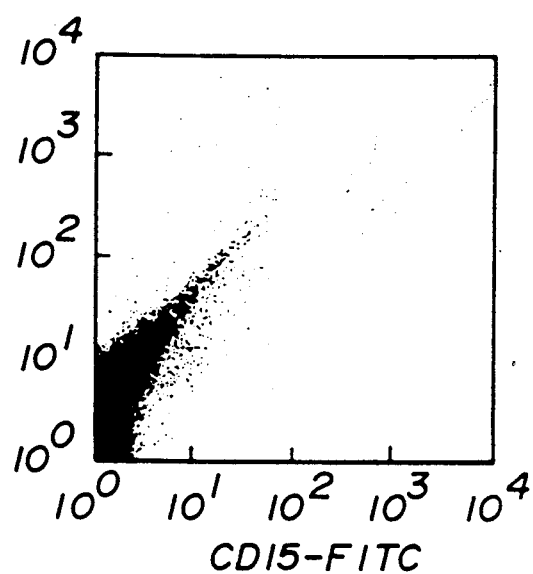
Figure 5A:
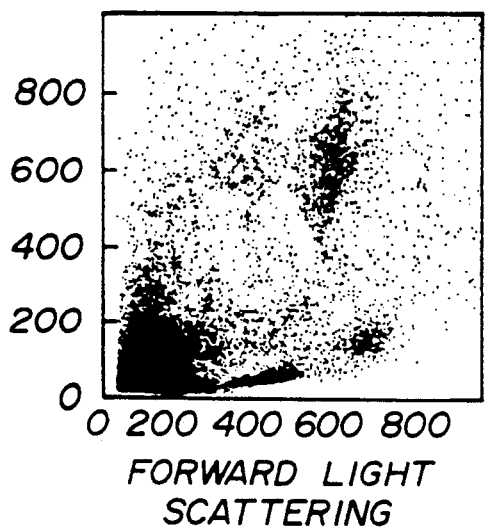
FIGS. 5A-5E comprise several dot plots as in FIG. 1 but wherein the cells also were stained with CD11b(PE) and CD15(FITC)
Figure 5B:
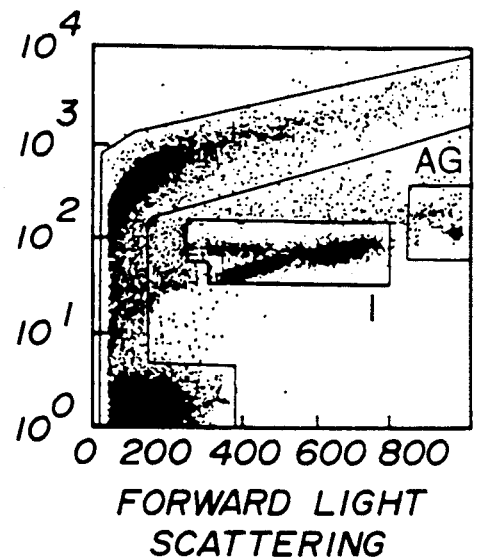
Figure 5C:
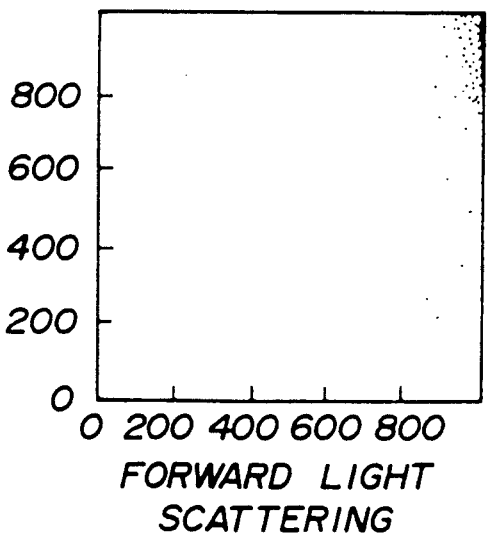
Figure 5D:
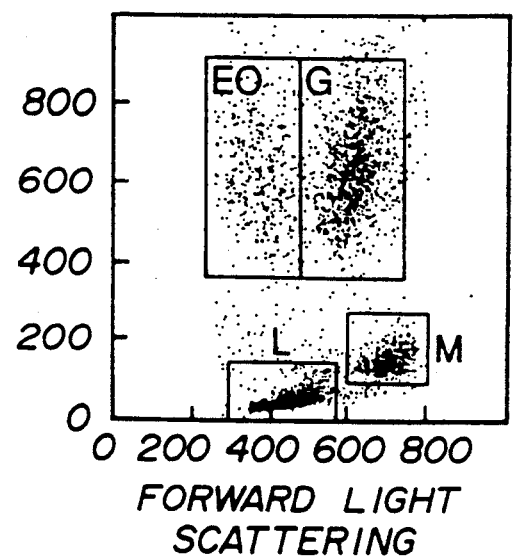
Figure 5E:
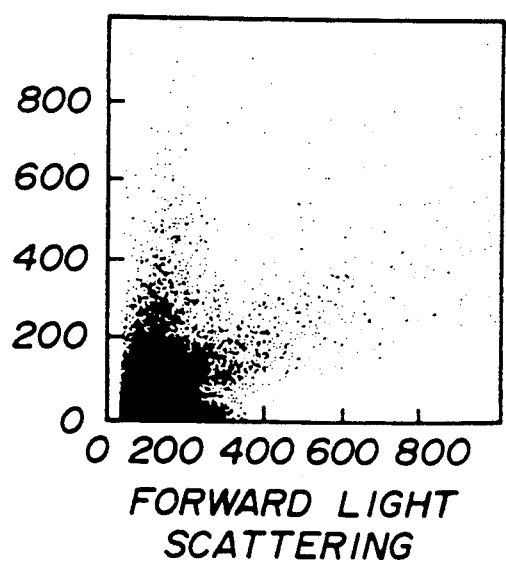
Figure 6A:
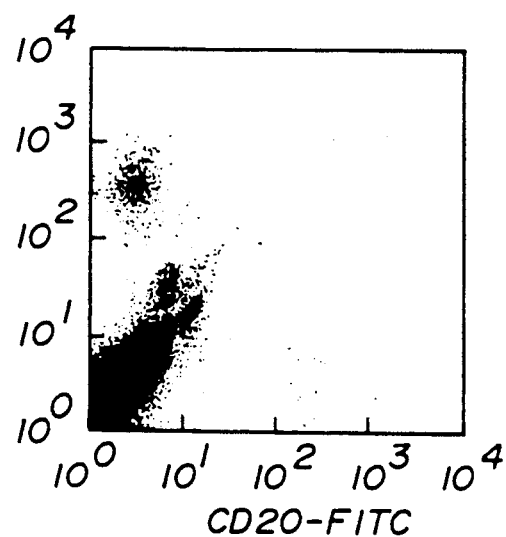
FIGS. 6A-6E comprise several dot plots of log CD11b(PE) fluorescence vs. log CD15(FITC) fluorescence (A,C-E) and log LDS-751 fluorescence vs. FLS (B) for the fixed PBL from erythrocyte depleted whole blood as shown in FIG. 5.
Figure 6B:
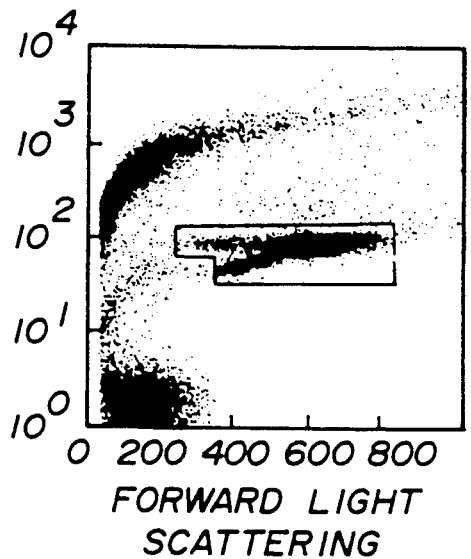
Figure 6C:
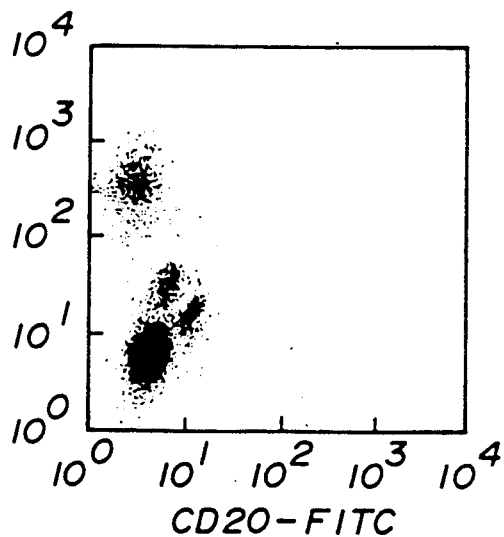
Figure 6D:
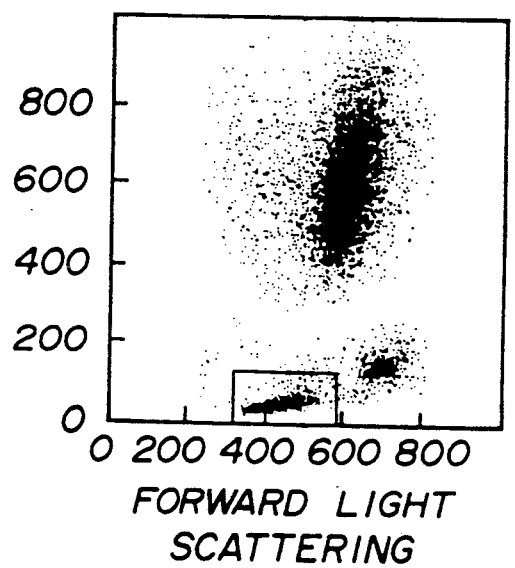
Figure 6E:
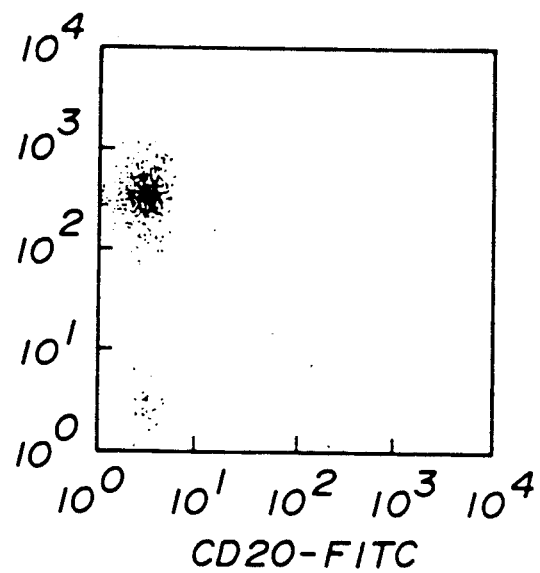

PBL were prepared using NH4Cl without subsequent fixation. The light scattering characteristics of this sample are shown in FIG. 2A. The cells that are identified as viable using FDA can also be distinguished based on LDS-751 fluorescence. See FIG. 2C. Greater than 98% of the cells were identified as positive by both FDA and LDS-751 fluorescence.

In a similar experiment, the unfixed cells were held for 48 hours after the NH4Cl lysis in order to increase the dead cells in the sample before staining with LDS-751 and FDA. FIG. 3. At this time, only 71% of the cells were viable based on FDA and LDS-751 fluorescence. By gating on the LDS-751 and light scattering, FIG. 3B, essentially all of the viable cells are included (98.5%) and only a few (8.6%) were dead based on FDA fluorescence. These data confirm that LDS-751 discriminates intact from damaged cells both in a viable state and after fixation.

EXAMPLE III

Combination of Immunofluorescence with LDS-751

The excitation of LDS-751 at 488 nm and its far red emission permits the combination of this dye with both FITC and PE immunofluorescence reagents. Spectral compensation must be used between the dyes to correct for PE emission entering the LDS channel (10% subtraction), however, only a minimal correction must be made in the other direction (2% subtraction). No compensation was required between the FITC and LDS-751 channels.

The advantage of using LDS-751 to identify damaged cells during lymphocyte subpopulation analysis is demonstrated in FIG. 4. In this example the erythrocyte lysed, whole blood was reacted with CD5(PE) (T-cells and a subpopulation of B-cells) and with CD20(FITC) (B cells). The intact cells were identified in the correlation between LDS-751 and forward light scatter. See FIG. 4B. The relatively infrequent population of CD5+/CD20-, CD5+/CD20+ and CD5-/CD20+ lymphocytes, FIG. 4E, can be identified by further gating on the forward and orthogonal light scattering. See FIG. 4D. By gating only on light scattering without identifying intact cells, the proportion of double labelled CD5+, CD20+ cells was increased by 50%. See FIG. 4C.

A second example illustrating the importance of combining immunofluorescence with the identification of intact cells is shown in FIG. 5 and 6. The cells in this example were labelled with CD15(FITC) and CD11b(PE). These different cell types labelled (i.e., monocytes, granulocytes and NK cells) can be distinguished based on quantitative differences in antibody labelling and on the differences in their light scattering characteristics. The CD15 MAb is known to agglutinate neutrophils since it is of the IgM isotype and the number of antigen sites on the target cells is high. This agglutination can be observed by comparing the relative frequency of the neutrophils, FIG. 5A and FIG. 1A, since these samples were obtained from the same cell preparation. It is evident that fewer neutrophils were observed by light scattering in the sample which was reacted with the CD15 MAb. It could be shown that the cells are still within the sample. As shown before, the intact cells, FIG. 5B (Population I), could be distinguished from the more brightly labelled larger cells identified in Population AG. These agglutinated cells comprising 20% the intact cell population had light scattering characteristics which were off scale in FIG. 5C.

The immunofluorescence of these cell populations is shown in FIG. 6. The agglutinated cells have the highest binding of both CD15 and CD11b. See FIG. 6C. These data indicate that the intensity of staining LDS- 751 could also be used to identify doublets or agglutinated cells within the sample.

The discrimination between cell population based on CD15 and CD11b binding was more easily observed when the damage cells and doublets were removed from the sample by getting the list mode file. The multiple populations identified by immunofluorescence were also recognizable by light scattering. In comparing FIG. 5D and 6D, the population which are mapped by the immunofluorescences have corresponding light scattering characteristics (L,M,N,EO). The neutrophils (N) and eosinophils (EO) were separated by both forward angle light scattering and by the intensity of CD15 fluorescence. The monocytes (M) were distinguished from the lymphocytes (L) both by their light scattering properties and CD11b expression. The NK cells (included in the L Population) expressed CD11b but did not express CD15 as did the monocytes (M). The identity of these cell populations has been confirmed by sorting the cells for morphological analysis.

A kit comprising containers separately containing a nucleic acid dye and one or more MAbs may be used in the practice of this invention. In the preferred embodiment, one container in the kit will contain LDS-751. Other containers in the kit may include separately any of the MAbs previously described in the above-examples. It will be appreciated by those skilled in the art that the MAbs may be labelled before inclusion in the kit or separate containers containing the fluorochromes may be included for independent labelling.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed:

1. A method for discriminating between a heterogeneous population of intact and damaged cells in a peripheral blood sample comprising the steps of:
   a) taking a sample of peripheral blood from an individual;
   b) adding to the sample one or more monoclonal antibodies to cell surface antigens, wherein the monoclonal antibodies are labeled with fluorescent labels and wherein the fluorescent labels have peak emission spectra that are distinguishable from each other and from a nucleic acid dye;
   c) adding a fixative to the sample;
   d) adding to the sample a nucleic acid dye which preferentially binds DNA, wherein the nucleic acid dye comprises the formula

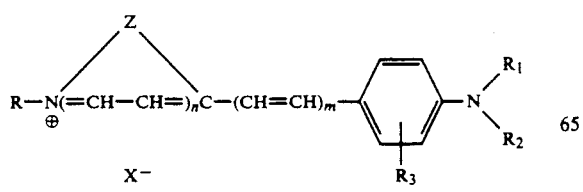

wherein
   n is 0;
   m is 1;
   R is a lower alkyl;
   $R_1$ and $R_2$ are lower alkyls;
   $R_3$ is hydrogen;
   Z is a quinoline nucleus which may be substituted with lower alkyl, halo, nitro, amino and dialkylamino; and
   X represents an anion;
   e) analyzing the sample in an automated instrument capable of passing the cells in the sample through a sensing region substantially one at a time and capable of detecting and recording both fluorescence and light scattered in more than one direction by each cell passing through said sensing region; and
   f) discriminating between damaged and intact cells in the sample based upon relative fluorescence intensity of the nucleic acid dye in each cell and light scattered.

2. The method of claim 1 wherein erythrocytes in the sample are lysed.

3. The method of claim 1 wherein the automated instrument is a flow cytometer.

4. The method of claim 1 wherein the fixative is paraformaldehyde.

5. The method of claim 1 wherein the fluorescent label is fluorescein isothiocyanate.

6. The method of claim 1 wherein the fluorescent label is phycoerythrin.

7. The method of claim 1 wherein the fluorescent labels are fluorescein isothiocyanate and phycoerythrin.

8. The method of claim 1 wherein the intact and damaged cells are further discriminated based upon relative fluorescence intensity of fluorescent labels and light scattered.

9. A method for discriminating between a heterogeneous population of intact and damaged cells in a peripheral blood sample comprising the steps of:
   a) taking a sample of peripheral blood from an individual;
   b) lysing erythrocytes in the sample;
   c) adding to the sample one or more monoclonal antibodies to cell surface antigens, wherein the monoclonal antibodies are labeled with fluorescent labels and wherein the fluorescent labels have peak emission spectra that are distinguishable from each other and from a nucleic acid dye;
   d) adding paraformaldehyde to the sample;
   e) adding to the sample a nucleic acid dye which preferentially binds DNA, wherein the nucleic acid dye comprises the formula

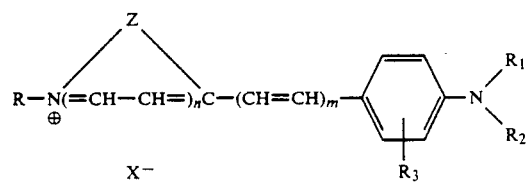

wherein
   n is 0;
   m is 1;
   R is a lower alkyl;
   $R_1$ and $R_2$ are lower alkyls;
   $R_3$ is hydrogen;

Z is a quinoline nucleus which may be substituted with lower alkyl, halo, nitro, amino and dialkylamino; and X represents an anion;

e) analyzing said sample in a flow cytometer equipped with a single laser tuned to 488 nm; and f) discriminating between damaged and intact cells in the sample based upon relative fluorescence intensity of the nucleic acid dye in each cell and light scattered.

10. The method of claim 9 wherein the intact and damaged cells are further discriminated based upon relative fluorescence intensity of fluorescent labels and light scattered.

* * * * *